(12) United States Patent
Koehler (10) Patent No.: US 8,088,228 B2
(45) Date of Patent: Jan. 3, 2012

(54) METHOD AND SYSTEM FOR CLEANING FLUID RESERVOIR OF VASCULAR ACCESS DEVICE

(75) Inventor: Cleve S. Koehler, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/768,851

(22) Filed: Apr. 28, 2010

(65) Prior Publication Data

US 2011/0265826 A1   Nov. 3, 2011

(51) Int. Cl.
*B08B 9/027* (2006.01)

(52) U.S. Cl. ..... 134/22.11; 134/1; 134/22.1; 134/22.12; 134/22.18; 134/34; 134/42; 606/108; 604/93.01; 604/288.01; 604/288.02; 604/288.03; 604/288.04; 604/500; 604/891.1

(58) Field of Classification Search ............. 134/1, 22.1, 134/22.11, 22.12, 22.18, 34, 42; 606/108; 604/93.01, 288.01, 288.02, 288.03, 288.04, 604/500, 891.1

See application file for complete search history.

(56) References Cited

U.S. PATENT DOCUMENTS

| 5,399,168 | A | 3/1995 | Wadsworth, Jr. et al. ..... 604/175 |
| 7,097,637 | B2 | 8/2006 | Triplett et al. ................ 604/192 |
| 7,351,233 | B2 | 4/2008 | Parks ...................... 604/288.01 |
| 7,431,728 | B2 | 10/2008 | Gerry et al. .................. 606/169 |
| 2005/0170070 | A1* | 8/2005 | Layrolle et al. ................ 427/2.1 |
| 2006/0224129 | A1 | 10/2006 | Beasley et al. ........... 604/288.01 |

* cited by examiner

*Primary Examiner* — Bibi Carrillo
(74) *Attorney, Agent, or Firm* — Brinks Hofer Gilson & Lione (57) ABSTRACT

A method and system for cleaning foreign material from a fluid reservoir of an implantable medical device, the fluid reservoir being substantially enclosed in an interior portion of the implantable device and accessible from an environment exterior of the implantable device through a penetrable septum. An elongated member having a first end and a second end is engaged with a source of ultrasonic energy capable of imparting vibrations to the first end. The septum is penetrated by the elongated member in a manner such that the first end extends into the fluid reservoir, and the second end does not extend into the reservoir. The ultrasonic energy source is activated to impart vibrations into the reservoir via the elongated member first end, in an amount sufficient to break up the foreign material into particulates, which can then be removed from the reservoir.

16 Claims, 6 Drawing Sheets

METHOD AND SYSTEM FOR CLEANING FLUID RESERVOIR OF VASCULAR ACCESS DEVICE

BACKGROUND

1. Technical Field

The present invention relates generally to a method and a system for cleaning an interior reservoir of an implantable medical device, and more particularly, to a method and system for ultrasonic cleaning of a fluid reservoir of a vascular access device.

2. Background Information

Implantable medical devices are widely used in the medical field to enable recurrent access to internal body portions of a patient. One common example of such an implantable medical device is a vascular access device (VAD). A VAD typically includes an implantable body containing a fluid reservoir, or chamber, and a self-sealing septum that provides controlled access to the reservoir.

A VAD is implanted in a pocket formed in the anatomy of the patient. A catheter extends from a connector tube portion of the device for providing fluid communication with the vascular system (i.e., an artery or vein) of the patient. Typically, a non-coring needle is utilized to puncture the skin, and provide access to the fluid reservoir of the VAD through the septum. The reservoir fluidly communicates with the catheter, and thereby, with the artery or vein.

An implanted vascular access device is particularly useful when prolonged, repeated, and/or targeted injection of medications is required, thereby sparing a patient the constant search for a suitable vessel to achieve vascular access. Moreover, the use of the VAD obviates the need for a dressing to cover the access site, once the incision from implantation of the device heals. One common example of the use of a VAD is the infusion of therapeutic agents during chemotherapy. In such use, infusion of the therapeutic agent(s) may be optimized by controlling the amount, timing, and location in the body of drug dosing. In addition to the use of VADs for infusion as described, such devices are also useful for supplying blood products and nutrients into the vascular system, as well as for blood sampling.

Since recurrent access to the VAD is generally desired, the device is typically implanted in a subcutaneous pocket at a location that is readily accessible to a needle. Once implanted, the catheter extends from the connector tube of the vascular access device to a remote target site for providing repeatable access to the patient's vascular system. The device will generally be placed at a location in which it can be supported by the underlying bony structure, and at a location which is convenient and comfortable to the patient.

A complication that may be encountered with the use of a VAD or like implantable device is the accumulation of foreign materials, such as thrombus and sludge, in the interior reservoir of the device. When present, such foreign materials can occlude the reservoir, thereby interfering with the smooth flow of fluids into and out of the device. When such materials build-up to an excessive level, fluid flow can be prevented altogether, thereby rendering the device useless. When the flow of fluid is interrupted to the extent that satisfactory flow is no longer possible, it is generally necessary to surgically remove an occluded VAD, and replace it with a new unit. This action results in added expense, and in increased trauma to the patient.

It would be desirable to provide a method and a system for cleaning an interior reservoir of an implantable medical device, such as a vascular access device, while the device remains implanted in the patient.

SUMMARY

The present invention addresses the shortcomings in the prior art. In one form, the invention comprises a method for cleaning foreign material from a fluid reservoir of an implantable medical device, wherein the fluid reservoir is substantially enclosed in an interior portion of the implantable medical device and accessible from an environment exterior of the implantable medical device through a penetrable septum of the device. An elongated member having a first end and a second end is provided. The elongated member is engaged with a source of ultrasonic energy capable of imparting vibrations to the first end of the elongated member. The septum is penetrated by said elongated member such that the first end extends into the fluid reservoir, and the second end does not extend into the reservoir. The ultrasonic energy source is activated to impart vibrations into the fluid reservoir via the elongated member first end, in an amount sufficient to break the foreign material into particulates. The particulates may then be removed, e.g., via suction, from the fluid reservoir.

In another form thereof, the invention comprises a system for cleaning foreign material from a fluid reservoir of an implantable medical device, wherein the fluid reservoir is substantially enclosed in an interior portion of the implantable medical device and accessible from an environment exterior of the implantable medical device through a penetrable septum of the device. An elongated member having a first end and a second end is sized such that the first end is capable of penetrating the septum and extending into the reservoir, and the second does not extend into the reservoir. A source of ultrasonic energy is in communication with at least the first end of the elongated member. The ultrasonic energy source is capable of transmitting sufficient ultrasonic vibrations to the first end for breaking up the foreign material into particulates, when the first end is extended into the reservoir. A source capable of introducing suction is provided for removing particulates from the reservoir.

In still another form thereof, the invention comprises a combination of an implantable vascular access device of the type having a fluid reservoir in an interior portion of the vascular access device, and having a self-sealing, penetrable septum covering said fluid reservoir, and a system capable of cleaning foreign material from the fluid reservoir. The system includes an elongated member having a first end and a second end, the elongated member sized such that the first end is capable of penetrating the septum and extending into the reservoir, and the second does not extend into the reservoir, and a source of ultrasonic energy in communication with at least the first end of the elongated member. The ultrasonic energy source is capable of transmitting sufficient ultrasonic vibrations to the first end for breaking up foreign material in the reservoir into particulates when the first end of the elongated member is extended into said reservoir. The system further includes a source capable of introducing suction in the reservoir for removing the particulates therefrom.

DETAILED DESCRIPTION OF THE DRAWINGS AND THE PRESENTLY PREFERRED EMBODIMENT

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of components of the system for cleaning foreign material from an implantable medical device. The term "proximal" is used in its conventional sense to refer to the end of the component that is closer to the operator during use. The term "distal" is used in its conventional sense to refer to the end of the component that is initially inserted into the patient, or that is closer to the patient during use.

Figure 1:
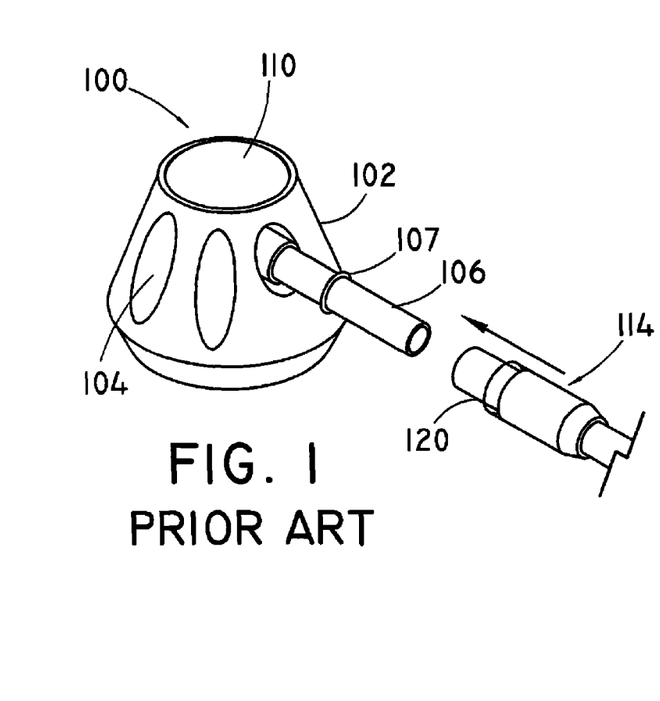
FIG. 1 is a perspective view of a conventional vascular access device and catheter.

FIG. 1 is a perspective view of a vascular access device 100 of a type that is well known in the art. VAD 100 includes an outer main body portion 102 formed of a biocompatible material, such as a plastic, a metal, or an assembly of plastic and metal components. The plastics may include various polymers, such as polysulfone or acetal polyoxymethylene (POM), and the metals may include titanium. Body portion 102 can be provided in a variety of sizes and shapes, such as the disk-like configuration shown in FIG. 1. Typically, body portion 102 ranges in dimension from, e.g., about 7 to 13 mm high to 19 to 31 mm long (up to 49 mm long for a double septum VAD).

Body portion 102 may include one or more suture holes 104. If desired, a physician may thread one or more sutures through suture holes 104 to ligate the device to body tissue, thereby inhibiting migration of the VAD after implantation. A septum 110 is provided along an upper surface of body portion 102. The septum can come in a variety of diameters, typically ranging from about 6 to 13 mm. The septum may be formed from a needle penetrable, self-sealing material, such as silicone, or other biocompatible elastomers known to be suitable for this purpose. Typically, a needle or cannula, (e.g., an infusion set needle) is utilized for penetrating the septum and gaining access to a fluid reservoir 108 (FIG. 2) positioned interiorly of body portion 102.

As illustrated in FIG. 1, a connector tube 106 extends radially from body portion 102. Connector tube 106 is in fluid communication with the fluid reservoir, and may include a beaded portion 107 or like structure along a length of the connector tube external of VAD body portion 102. Connector tube 106, and beaded portion 107, are sized and positioned to receive an end of a conventional catheter 120. Catheter 120 establishes fluid communication between a body vessel (not shown) and the fluid reservoir. In the version shown in the figure, a locking sleeve 114 is provided for locking catheter 120 over beaded portion 107 of the connector tube in well-known fashion.

Vascular access devices are well known in the medical arts, and the VAD 100 illustrated and described herein is merely one example of such devices. Additionally, some such devices may be provided with a second fluid reservoir and septum to increase the usefulness and versatility of the device. With minor modification, the invention described herein may be utilized in connection with any such devices, provided that the device includes at least one penetrable septum and fluid reservoir in the general nature of those described and/or illustrated herein. Devices suitable for use in conjunction with the present invention are commercially available from a variety of sources. One particularly preferred VAD for use in the inventive method is the VITAL-PORT® Vascular Access System, available from Cook Medical, Inc., of Bloomington, Ind. Such VADs are available in both single-septum and double-septum configurations.

Figure 2:
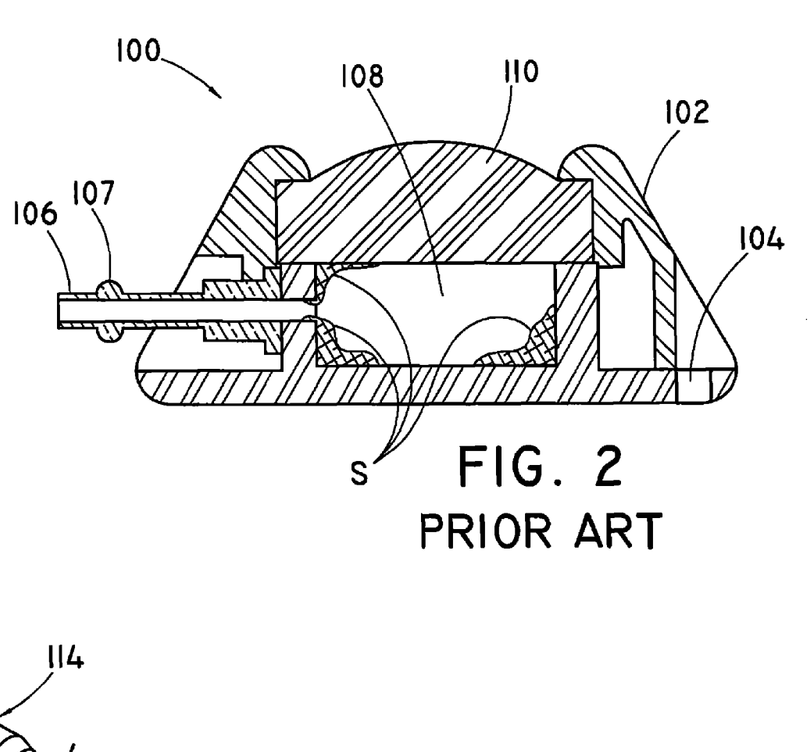
FIG. 2 is a cross-sectional view of the conventional vascular access device shown in FIG. 1, illustrating a build-up of sludge in the fluid reservoir of the device.

FIG. 2 is a cross-sectional view of the conventional vascular access device 100 shown in FIG. 1, illustrating the fluid reservoir 108 interiorly of body portion 102 of the VAD. A complication that may be encountered with the use of a VAD is the build-up of foreign material, such as sludge, thrombus, and other contaminants, in the fluid reservoir. One example of the manner in which such foreign material S may build up in the fluid reservoir 108 is shown in FIG. 2. In practice, the build-up of foreign material S in the fluid reservoir can be greater than, or less than, that illustrated in FIG. 2. Excessive build-up of foreign material, or build-up at critical portions of the reservoir, can occlude the fluid reservoir, and prevent the smooth flow of fluids through the reservoir. As stated above, when this occurs, it may be necessary to surgically remove the VAD, and replace it with a new unit. This adds unnecessary expense to the VAD treatment, and also adds trauma and inconvenience to the patient resulting from the surgical removal and replacement.

Figure 3:
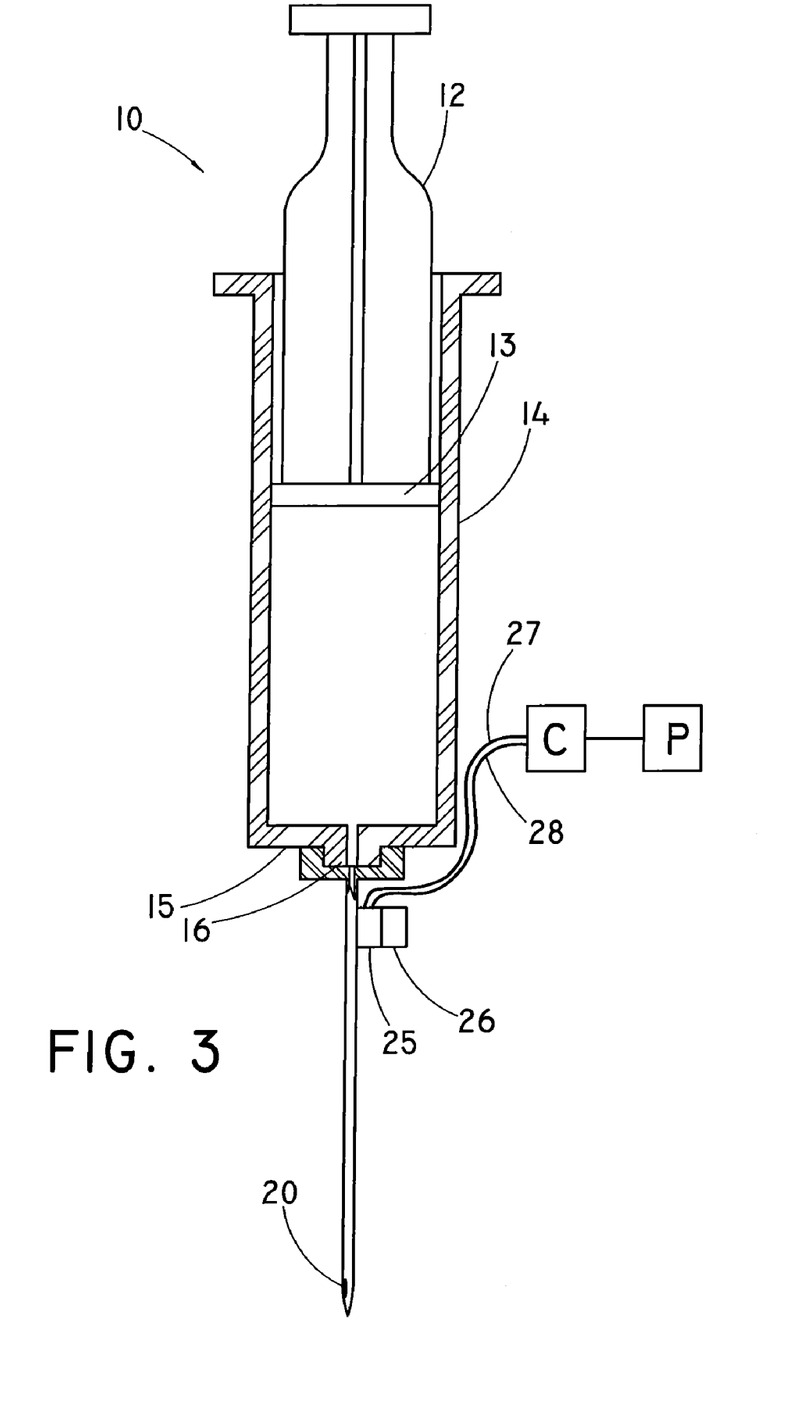
FIG. 3 is an enlarged side view, partially in section, of one embodiment of a system for breaking up foreign material from the fluid reservoir of an implantable medical device, according to the present invention.

FIG. 3 is a side view, partially in section, of one embodiment of a system for breaking up foreign material S from the fluid reservoir of an implantable medical device, such as a vascular access device, according to the present invention. In the embodiment shown, the inventive system comprises a syringe 10 that is configured in a manner such that ultrasonic vibrations may be transmitted into the fluid reservoir of the VAD, as further discussed herein. Syringe 10 may be of conventional construction having a movable plunger 12, and a barrel 14 sized for receiving plunger 12 in well-known fashion. Syringe barrel 14 may be formed of typical compositions, e.g., polymers and other materials (e.g., stainless steel) commonly used for such purposes, and may have a volume of, for example, 20 to 100 ml.

Typically, plunger 12 terminates at an end 13. As shown, end 13 is sized and positioned within barrel 14 in a manner suitable for expelling fluids from the barrel in well-known fashion. A needle 20 is engaged at the outlet end of the syringe. Needle 20 may be engaged with syringe 10 in any conventional fashion, e.g., by a screw fit or a snap fit to an extension portion 16 at an otherwise closed end 15 of syringe barrel 14.

Needle 20 may be of a type and dimension conventionally used for penetrating a septum, such as a VAD septum. Preferably, needle 20 comprises a non-coring needle, such as a Huber needle. Those skilled in the art are aware that a non-coring needle is capable of penetrating a substrate without removing material from the substrate (i.e., without creating a core). In non-coring needles the open distal port of the needle is typically provided along the axial side at the distal end of the needle, rather than as an opening at the extreme distal tip (i.e., bottom) of the needle as is more common with conventional needles. Although non-coring needles may require more force to penetrate the skin than other needles, the use of such needles is beneficial because by not creating a core upon entry, it extends the longevity of the VAD septum.

Although needles of virtually any dimensions may be utilized, the dimensions for such a needle are preferably between about 19 and 22 gauge, and having a length between about 25 and 50 mm. Generally, at least the distalmost 5 to 10 mm of the needle will extend into the fluid reservoir 108 upon insertion. For use herein, needle 20 is preferably formed of a composition, such as a metal or a metal alloy, capable of transmitting vibrations into the fluid reservoir, in a manner to be described. One particularly preferred needle composition that is capable of transmitting such vibrations is stainless steel.

A source capable of providing ultrasonic energy to the needle is provided. In the embodiment shown, the ultrasonic energy is provided by an ultrasonic transducer 25 that is directly engaged with needle 20, e.g., via an adhesive. As shown, a resonating mass 26 is securely engaged with transducer 25 in well-known fashion. Transducer 25 is electrically connected, e.g., via conventional power cords 27, 28, with a conventional controller C, and thereby, with a power unit P. Controller C and power unit P are schematically shown in FIG. 3. The power unit is preferably powered by a conventional electrical source, such as standard 120 V, 60 Hz electricity, and the power is transmitted to controller C by a suitable cord in well known fashion. Upon demand, controller C is capable of providing a controlled amount of power to the transducer, which controlled amount of power may preferably be varied as desired.

Preferably, transducer 25 comprises a well-known piezoelectric unit. Those skilled in the art will appreciate that the piezoelectric component may be formed from conventional materials commonly utilized for such purpose, such as piezoelectric ceramic compounds. Resonating mass 26 typically comprises a dense material, such as a metal or metal alloy (e.g., stainless steel), of a type commonly used for enhancing the vibrations created by the transducer, to thereby assist breakage of the sludge in fluid reservoir 108 as described herein. Preferably, resonating mass 26 is securely attached to the transducer, e.g., by an epoxy or other adhesive. Upon activation, transducer 25 is capable of vibrating the mass 26 at a rate between about 15 and 400 kHz, and more preferably, between about 20 and 80 kHz. As the transducer vibrates the mass, the mass creates pressure waves in the fluid in known manner. As the fluid transmits the waves, a small implosion-like event is created near a hard surface that frees contaminates from the port.

Figure 4:
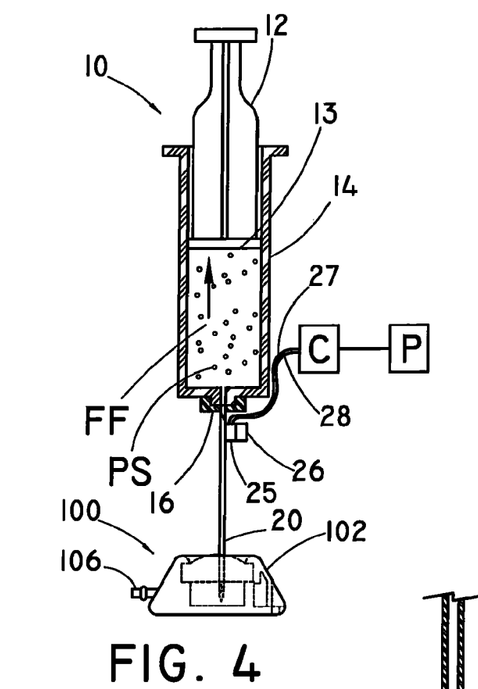
FIG. 4 is a side view of the system of FIG. 3, partially in section, illustrating a needle extending through the septum of the implantable medical device.
Figure 4A:
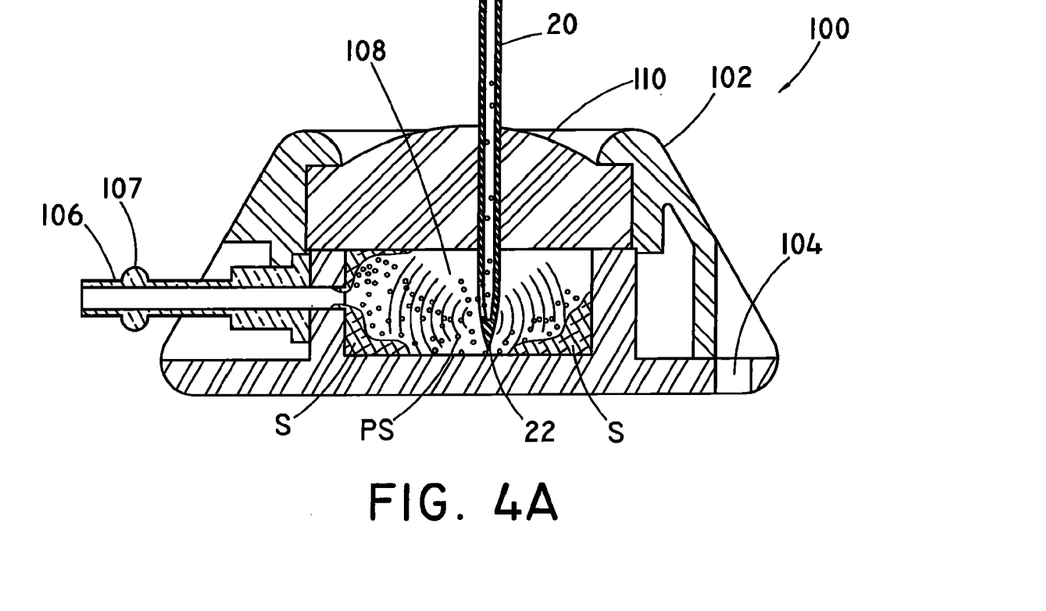
FIG. 4A is an enlarged sectional view of a portion of FIG. 4, illustrating the vibrating distal tip of the needle in the fluid reservoir.

FIG. 4 shows syringe 10 mounted to a conventional vascular access device, such as VAD 100 in FIGS. 1 and 2. FIG. 4A is an enlarged view of a portion of FIG. 4, illustrating the vibrating distal tip of the needle in the fluid reservoir 108 of the VAD. As illustrated, a first, or distal, end 22 of non-coring needle 20 penetrates septum 110, and extends therethrough into the fluid reservoir. The vibrations generated by the ultrasonic transducer 25 cause needle 20 to vibrate at a controlled frequency. These vibrations are transmitted into the fluid reservoir 108, to cause foreign material S to be broken into particulates PS.

In use, it is preferred that a portion of barrel 14 of syringe 10 includes a flushing fluid FF. When plunger 12 is advanced in a downward direction (as oriented in FIG. 4), the flushing fluid is expelled from the syringe through needle end 22, and into fluid reservoir 108. Alternatively, a flushing fluid may be introduced into the reservoir through a separate needle or cannula (not shown). Preferably, the flushing fluid is heparinized saline. Other physiologically acceptable fluids, such as aqueous-based additives or soaps, may be substituted for, or used in conjunction with, heparinized saline. During use, the physician should monitor the amount of flushing fluid inserted into the reservoir, to prevent sludge from the fluid reservoir from passing out of the catheter into the vessel.

As indicated above, the ultrasonic vibrations introduced into the fluid reservoir are of a frequency sufficient to break up the foreign matter (e.g., sludge) S built up within the fluid reservoir 108 into particulates PS. Once the foreign matter is broken up into the particulates PS, it is desirable to remove the particulates from the reservoir. Thus, a suction force can be applied to the reservoir to remove these particulates. Conveniently, when a syringe 10 has been utilized to supply the flushing fluid and/or to apply the vibrations as shown in FIG. 4, the suction can be applied by merely withdrawing plunger 12 back through the barrel of the syringe (i.e., in an upward direction in the orientation of FIG. 4). As the plunger is withdrawn, fluid from reservoir 108 containing particulates PS is withdrawn into syringe barrel 14. The withdrawn fluid can be collected from the syringe barrel and disposed of in a suitable disposal container (not shown) in any convenient fashion.

The cleaning process as described above can be repeated as often as desired. When the withdrawn fluid from a particular flushing, vibrating, and withdrawal sequence has a lesser amount of particulates PS than a previous sequence, it is indicative that the amount of particulates in the fluid chamber has been reduced. The physician can determine when a suitable amount of cleaning has occurred. Thus, for example, if upon a subsequent attempt to withdraw blood from the fluid reservoir of the VAD, the physician determines that the attempted withdrawal is difficult, incomplete, or includes an undesirably large amount of particulates, the physician can simply repeat the cleaning process one or more additional times. During such subsequent steps, the ultrasonic energy can be applied at the same vibration intensity and frequency as before, or if desired, at a higher or lower setting for intensity, frequency, or combination of both by use of the controller.

The syringe, needle, and transducer arrangement as shown in FIGS. 3 and 4 represent merely one example of a suitable arrangement for carrying out cleaning of the fluid reservoir via ultrasonic vibrations. Those skilled in the art will appreciate that other suitable arrangements may be substituted, and are considered within the scope of the invention.

For example, those skilled in the art will appreciate that the manner by which ultrasonic energy may be applied to the needle need not necessarily be provided by a unit comprising transducer and mass 25, 26 arranged along the length of the needle, as shown in FIGS. 3 and 4. As one alternative, the arrangement of the transducer and mass 25, 26 along the length of the needle may be replaced with a single donut-type transducer that encircles the needle, rather than being engaged along the side of the needle. In this arrangement, the transducer 25 surrounds and is affixed to the needle. Mass 26 is then positioned concentrically around the transducer. This arrangement may be capable of providing increased vibration to the needle when compared to the arrangement of FIGS. 3 and 4, thereby enhancing the cleaning energy of the device.

As another alternative, a second transducer and mass unit may also be engaged along the length of needle 20, in order to increase the vibrating capability of the needle. When present, the second transducer and mass unit may be engaged with needle 20 in the same general fashion as the transducer and mass 25, 26 illustrated in FIG. 3, but aligned at a different vertical position along the length of the needle. Alternatively, the second transducer and mass unit 25, 26 may be aligned at the same or a similar vertical position as the transducer and mass shown, but on the opposing (longitudinal) side of the needle.

As yet another alternative, the transducer and mass unit need not necessarily be directly engaged with the needle. Rather, the transducer can alternatively be engaged with other portions of the inventive system, as long as the arrangement is capable of imparting sufficient vibrations to break up the foreign material S. For example, a transducer and mass unit can be engaged along the side of the syringe barrel 14. As still another alternative, the transducer and mass may be engaged with the plunger, e.g., in a manner such that it extends in a downward direction from plunger end 13. In these and other alternatives, the transducer must be mounted in a manner such that sufficient vibration can be transmitted to the needle to break up the sludge in the fluid reservoir. As still another alternative, any of the above arrangements may be combined. Thus, for example, a transducer and mass can be arranged along the needle as shown in FIGS. 3 and 4, and another transducer and mass arrangement can be arranged along the side of the syringe.

Although such alternative mounting arrangements are possible, it is believed that optimal vibration is achieved when the transducer is engaged with the needle, as shown in FIGS. 3 and 4. When such alternate mounting arrangements are carried out, those skilled in the art will appreciate that any feature of the inventive system (e.g., the barrel and/or plunger end) having a transducer affixed thereto should be formed of a composition, such as a metal or metal alloy (e.g., stainless steel) capable of transmitting sufficient vibrations into the fluid reservoir to break up the foreign material S.

Figure 5:
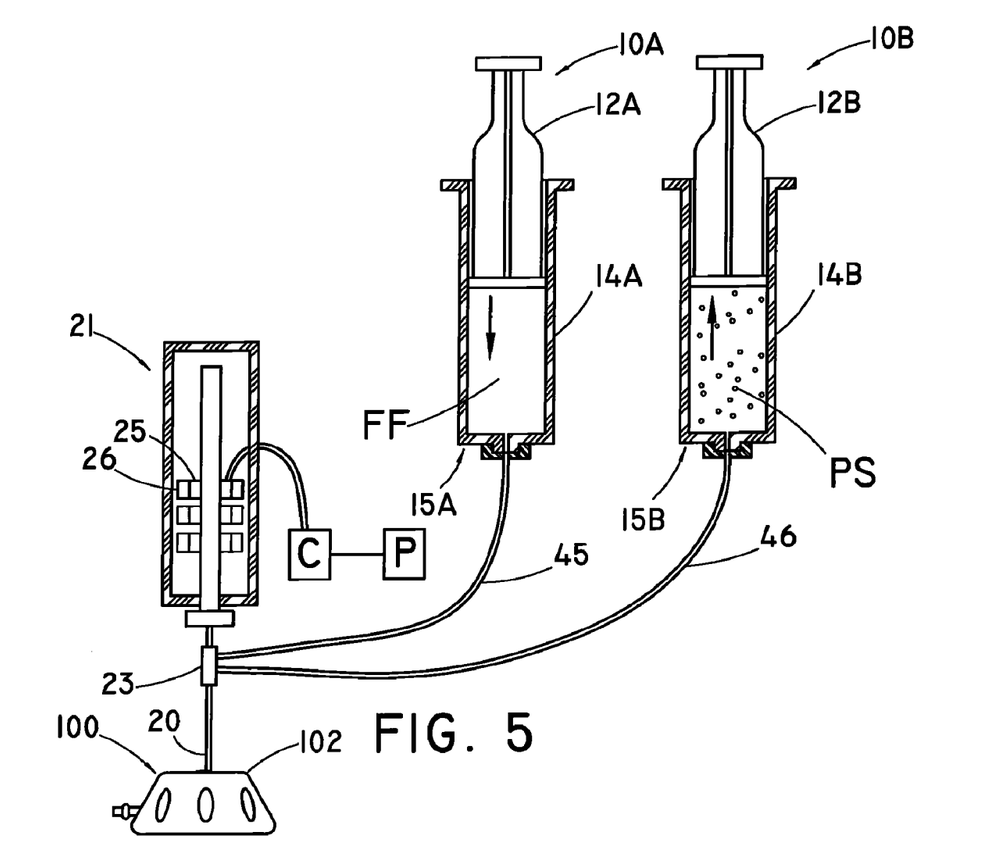
FIG. 5 illustrates a variation of the system of FIGS. 3 and 4, partially in section, wherein the system includes first and second syringes 10A, 10B.

FIG. 5 illustrates another variation of the embodiment of FIGS. 3 and 4. This embodiment utilizes two syringes, 10A, 10B, each of which is in fluid communication with needle 20. Needle 20 includes a needle handle 21 that is sized to enable it to be easily grasped and controlled by the physician. One or more transducer and mass units 25, 26 (three donut-type units are shown in section in the figure) may be aligned along the proximal end of needle. In the non-limiting example shown, the donut-shaped transducer units 25, 26 are positioned around the proximal end of the needle 20, which end is received within a bore of needle handle 21. The transducer units may be powered and controlled by respective power and controller units P,C, as shown schematically in FIG. 5.

In this embodiment, an inner cannula 44 extends through the bore of needle 20 and into the fluid reservoir 108. Inner cannula 44 is preferably polymeric, e.g., PET or nylon, and has an outer diameter suitable to permit entry into the bore of needle 20. When utilized with a 19 to 22 gauge needle as described, inner cannula 44 has an outer diameter of about 0.010 to 0.020 inch. In this variation, the interior space of respective needle 20 and inner cannula 44 are maintained at different pressures.

A hub 23 is disposed along the proximal length of needle 20. Typically, hub 23 is formed (e.g., via injection molding) to include a pair of distinct passageways (not shown) extending therethrough in well-known manner. One such passageway receives the distal end of a conduit 45 that extends from bottom portion 15A of syringe 10A. The other passageway receives the distal end of a conduit 46 that extends from bottom portion 15B of syringe 10B. With this arrangement, fluid communication may be effected between the interior of syringe 10A and the interior space of needle 20. Similarly, fluid communication may be effected between the interior of syringe 10B and the interior space of inner cannula 44.

In this embodiment, a flushing fluid FF (e.g., heparinized saline) is introduced into the barrel 14A of syringe 10A. The flushing fluid is pumped into fluid chamber 108 by depressing syringe plunger 12A, in the manner described above. The flushing fluid FF advances through syringe barrel 14A, conduit 45, needle 20 (via hub 23), and thereafter into fluid chamber 108. The direction of entry of the flushing fluid into the fluid chamber is shown by the arrows in FIG. 5.

Figure 5A:
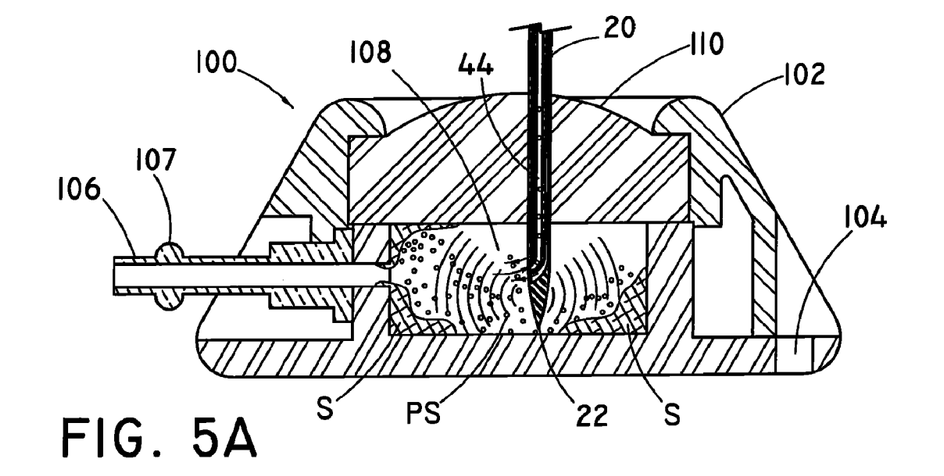
FIG. 5A is an enlarged sectional view of a portion of FIG. 5, illustrating the vibrating distal tip of the needle in the fluid reservoir.

As shown in FIG. 5A, ultrasonic vibrations are introduced into the fluid chamber in the same manner as before, e.g., by vibrations imparted to the distal end of the needle 20 by transducer and mass 25, 26. As a result, foreign matter S in the reservoir is broken up in particulates PS. During and/or after exposure to the vibrations, suction is applied to the fluid reservoir through the bore of the cannula 44. In the embodiment shown, suction is applied by withdrawing plunger 12B in syringe barrel 14B. The suction forces generated are transmitted into fluid chamber 108 through conduit 46 and the interior space of inner cannula 44. Particulates PS are withdrawn into barrel 14B of syringe 10B via inner cannula 44, for removal to a disposal receptacle by well-known means. The respective flushing and withdrawal sequences can be repeated as many times as desired.

Those skilled in the art will appreciate that, with minor modification, the alignment of the passageways with the respective syringes illustrated in FIGS. 5 and 5A can be reversed. In this event, the flushing fluid can be introduced through the cannula 44, and the suction can be pulled through the needle bore. By utilizing two syringes in the arrangement of FIG. 5, the system is generally capable of continuous operation, and does not require disengagement of the syringe after each successive operation as in the previous example.

Figure 6:
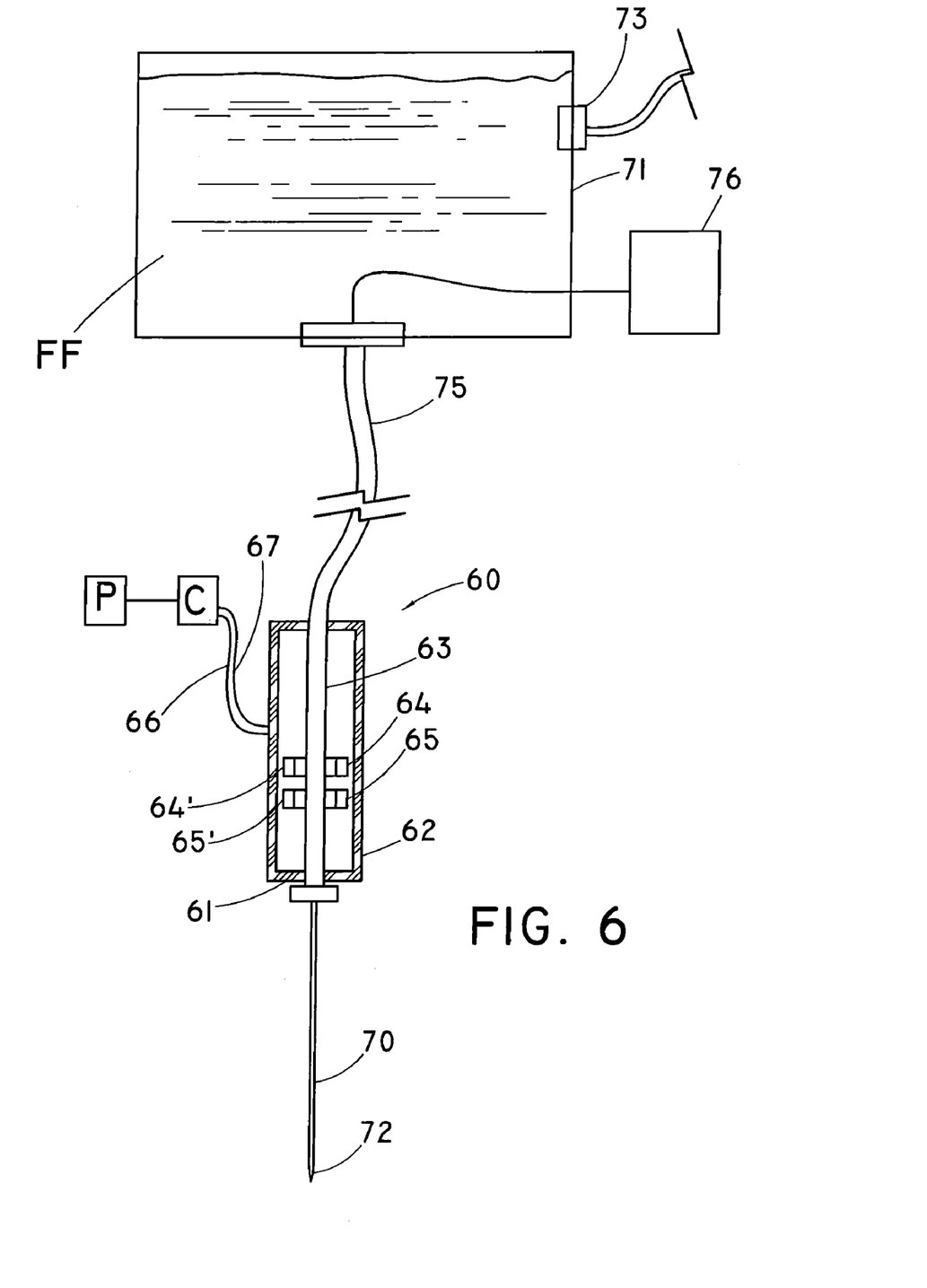
FIG. 6 is a side view of an alternative embodiment of a system for breaking up foreign material.

FIG. 6 is a side view of an alternative system that may be utilized for transmitting vibrations into the fluid reservoir of a VAD for breaking up sludge S. In this system, a generally hand-held device 60 is provided. Device 60 comprises a handle 62, and a tubular bore 63 extending longitudinally through handle 62. One or more transducers 64, 64' and resonating masses 65, 65' (two such units are shown in FIG. 6) may be disposed along tubular bore 63, and engaged with an interior of handle 62. Handle 62 has an outer diameter sized to enable the physician to comfortably grasp the unit with one hand.

In the embodiment shown, the transducer and mass units are securely engaged at the bore 63, e.g., via an epoxy or other adhesive. Although the transducer units and accompanying resonating masses are shown positioned along bore 63, this is not required, and the one or more transducer units and masses may alternatively be positioned along the length of needle 70, in any manner previously described with the aforementioned needle 20. Transducer units 64, 64' are electrically connected, via power cords 66, 67, with controller C, and thereby, with power unit P as before. When dual transducer units 64, 64' are present as shown in FIG. 6, a single set of power cords can extend from both transducer units to the controller, or alternatively, each unit can be engaged to the same or separate controllers by a separate set of power cords in well-known fashion.

Needle 70 may be integral with end 61 of handle 62. Alternatively, needle 70 may be attached to handle end 61 in any conventional fashion, such as by a screw fit or a snap fit as described above. Once again, it is desirable that the needle has a non-coring Huber-type distal end. Needle 70 preferably has a length similar to that of needle 20.

Device 60 is preferably aligned, via fluid conduit 75, in fluid communication with a receptacle 71 containing a flushing fluid FF. Preferably, the flushing fluid is introduced into receptacle 71 through inlet 73 under pressure, utilizing a conventional fluid pump. However, a separate pressure source for introducing the flushing fluid is not necessarily required, and suitable fluid pressure may alternatively be provided by the fluid in the line.

During use, distal end 72 of needle 70 is introduced into the fluid reservoir of the VAD as described above. Flushing fluid FF is passed into bore 63 under pressure via fluid conduit 75, and thereby, through needle 70 into the fluid reservoir. Ultrasonic vibrations of a frequency sufficient to break up the foreign matter S into particulates PS are introduced into the fluid reservoir 108 in the manner described previously.

Once the foreign matter is broken up into the particulates PS, it is desirable to remove the particulates from the reservoir. Thus, suction is applied through the hand-held device 60. Suction may be applied by disconnecting the conduit 75 from the flushing fluid, and connecting it to a source of suction, shown schematically in FIG. 6 as suction source 76. As stated above, any conventional source of suction may be applied, such as a syringe or a medical vacuum pump.

Although device 60 has been described as having a single bore 63 extending therethrough that is used for infusion of the flushing fluid and withdrawal of particulates PS, device 60 may alternatively be provided with dual bores. In this case, a first bore would be in communication with the flushing fluid for infusion, and a second bore would be in communication with the source of suction for withdrawal of the particulates. The bores may extend axially through device 60 in side-by-side fashion. Alternatively, the bores may be concentrically arranged, e.g., in the manner as shown in FIG. 5A. As still another alternative, a separate needle engaged with a suitable source of suction may be inserted into the fluid reservoir for removal of the particulates.

Figure 7:
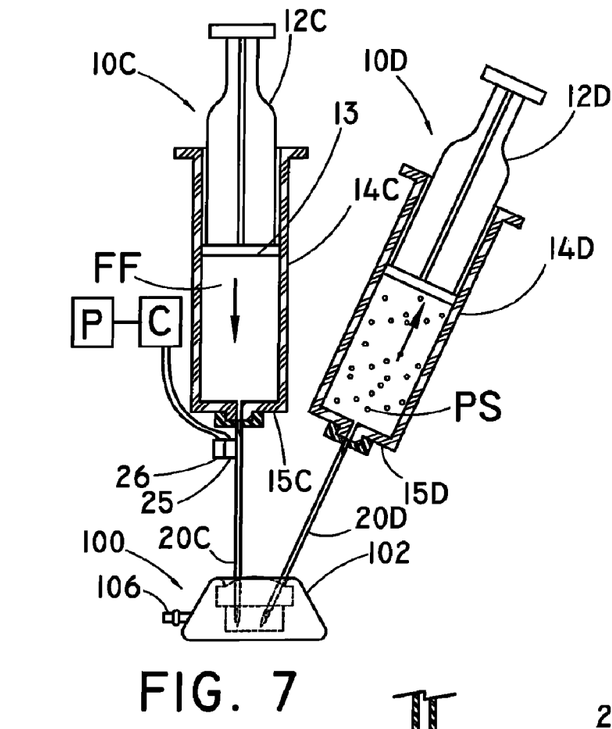
FIG. 7 is a side view, partially in section, of another embodiment of a system for breaking up foreign material utilizing first and second syringes 10C, 10D.
Figure 7A:
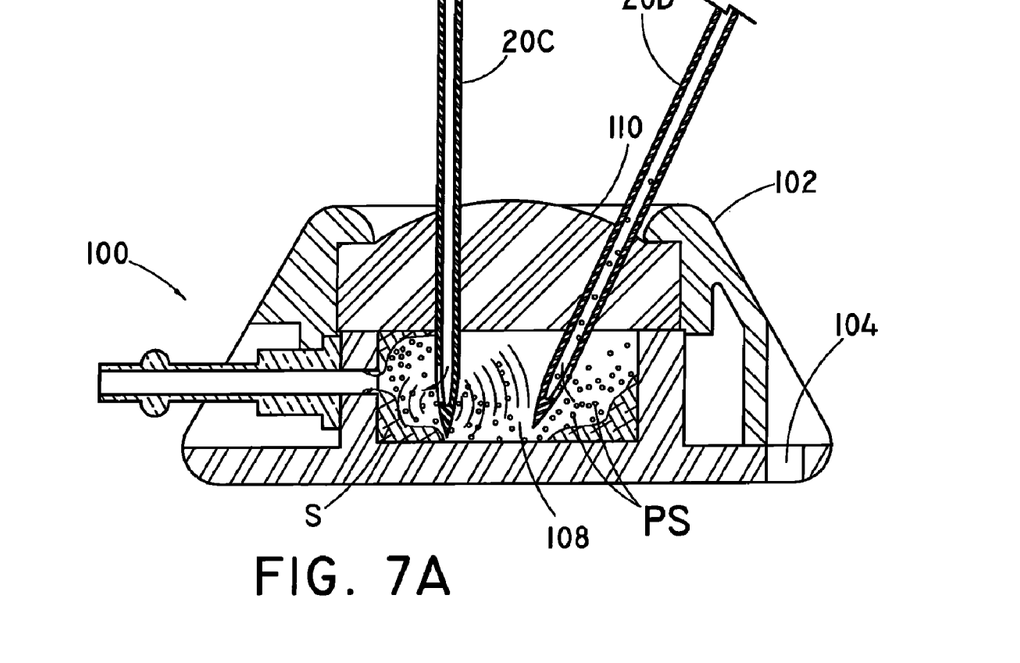
FIG. 7A is an enlarged sectional view of a portion of FIG. 7, illustrating the needle distal tips extending into the fluid reservoir.

FIGS. 7 and 7A illustrate another variation that utilizes two syringes, in this case syringes 10C, 10D. Each syringe has a respective plunger 12C, 12D, syringe barrel 14C, 14D, and syringe bottom portion 15C, 15D, as before. Preferably, a flushing fluid is introduced into syringe barrel 14C. Needles 20C, 20D extend from respective syringe bottom portions 15C, 15D in a manner described above. A transducer and resonating mass 25, 26 may be engaged with syringe 10C in any of the manners heretofore described. In the embodiment illustrated in FIG. 7, transducer and mass 25, 26 are engaged along the length of needle 20C. A controller C and power unit P are provided as described above.

In this variation, needles 20C, 20D are each passed through septum 110 of VAD 100 (FIG. 7A). Once again, it is preferred that needles 20C, 20D are non-coring needles (i.e., Huber needles). Preferably, the respective distal open ends of needles 20C, 20D do not face each other, so that the cleaning ability of the system is not compromised.

In use, plunger 12C is depressed, whereupon flushing fluid FF is expelled into fluid reservoir 108. Ultrasonic energy is transmitted into the fluid reservoir 108 through needle 20C, via controller C and power unit P as before. Once again, sufficient vibrations are induced into the fluid reservoir so that foreign matter S is broken into particulates PS. Once the particulates are formed, plunger 12D is withdrawn. This action creates a suction force in the fluid reservoir, whereby particulates PS are withdrawn into syringe barrel 14D via needle 20D. The particulates may then be disposed of by conventional means. By providing a separate inlet and outlet as described, better mixing/turbulence will likely occur, thereby leading to enhanced breakdown of the sludge material.

Although syringe 10 and hand-held device 60 as described above are provided with ultrasonic transmission capability, e.g., via engagement of the ultrasonic transducer and resonating mass to the needle or the barrel of the syringe, the vibrations may be imparted into the reservoir by other means. For example, a separate solid needle or probe may be engaged with a source of ultrasonic energy, e.g., via a transducer and resonating mass 25, 26 electrically connected to a controller C and power unit P as before. In this case, the solid needle or probe may be inserted through the septum into the fluid reservoir for imparting the vibrations. Use of a solid needle or probe may provide enhanced vibration into the fluid reservoir when compared to the vibrations emanating from a hollow needle. Once again, when a solid needle or probe is utilized, it is preferred to utilize a needle or probe having a non-coring distal (penetrating) end. Use of a solid needle or probe may also provide efficiency and cost benefits, as the needle or probe could be re-sterilized for multiple use.

If a solid needle or probe is utilized to transmit the vibrations into the reservoir, one or more conventional syringes having a needle tip may be utilized to inject a flushing fluid through the septum and into the fluid reservoir, and to withdraw the particulates from the reservoir. In this case, the needle need not be structured to transmit ultrasonic vibrations.

As another variation, a conventional syringe and hollow non-coring needle can be utilized to inject the flushing fluid as described. The non-coring needle can then be removed, and replaced with a solid probe or needle engaged with a suitable source of ultrasonic energy for imparting the vibrations into the reservoir. The solid probe or needle can be inserted into the fluid reservoir, whereupon the ultrasonic vibrations are activated to break up the foreign matter. The solid needle or probe can be removed, and a hollow needle can be re-applied for drawing suction. Following removal of the particulates, a final flush of the reservoir with heparinized saline may be carried out.

Although suction has generally been applied in the preceding examples via the upstroke of a syringe, those skilled in the art will appreciate that there are many alternative ways in which a suitable suction force may be generated. For example, it is well known in the medical arts to utilize medical vacuum pumps for withdrawal of fluids, as schematically shown, e.g., in FIG. 6. In this instance, rather than creating suction via the upstroke of the plunger, the medical vacuum pump can be arranged for drawing the suction. In this event, the vacuum pump may simply be fluidly connected to a receptacle for receiving the particulates and withdrawn fluids. Medical vacuum pumps suitable for such purpose are commercially available, e.g., from Mega Med (UAE). Such pumps may be conveniently engaged with the needle, and activated to withdraw the fluid and particulates for disposal in a separate receptacle.

Those skilled in the art will appreciate that applications of the present invention may be carried out utilizing variations and permutations not specifically described herein, and that may be arrived at without undue experimentation when applying the techniques described herein. All such variations and permutations are considered within the scope of the present invention.

It is therefore intended that the foregoing detailed description be regarded as illustrative rather than limiting, and that it be understood that it is the following claims, including all equivalents, that are intended to define the spirit and scope of this invention.

The invention claimed is:

1. A method for cleaning foreign material from a fluid reservoir of an implantable medical device, the fluid reservoir being substantially enclosed in an interior portion of the implantable medical device and accessible from an environment exterior of the implantable medical device through a penetrable septum of the device, comprising:
providing an elongated member having a first end and a second end;
engaging said elongated member with a source of ultrasonic energy capable of imparting vibrations to said first end;
penetrating said septum with said elongated member such that said first end extends into said fluid reservoir, and said second end does not extend into said reservoir; and
activating said ultrasonic energy source to impart vibrations into said fluid reservoir via said elongated member first end, in an amount sufficient to break up said foreign material into particulates.

2. The method of claim 1, wherein the implantable medical device comprises a vascular access device, further comprising the step of removing said particulates from the fluid reservoir of the vascular access device.

3. The method of claim 1, wherein said elongated member comprises a non-coring needle.

4. The method of claim 1, wherein said elongated member comprises a needle, said needle comprising said first and second ends and having a passageway therethrough, further comprising a cannula received within said needle passageway, said cannula having first and second ends, said respective needle and cannula first ends extending into said reservoir, said needle second end communicating with one of a source of flushing fluid for transmission into said reservoir and a source of suction for removing said particulates from said reservoir, and said cannula second end communicating with the other of said source of flushing fluid for transmission into said reservoir and said source of suction for removing said particulates; said method further comprising the steps of transmitting said flushing fluid into said reservoir to assist break up of said foreign material into said particulates, and removing said particulates from said reservoir via suction.

5. The method of claim 1, wherein said elongated member comprises a first hollow needle, further comprising a second hollow needle, the method further comprising the steps of:
penetrating the septum with respective first ends of said first and second needles, wherein the respective second ends of said needles do not penetrate said septum;
transmitting a flushing fluid into said fluid reservoir through one of said hollow needles to assist break up of the foreign material into said particulates; and
introducing a suction force into said fluid reservoir through the other of said hollow needles to extract said particulates.

6. The method of claim 1, wherein said ultrasonic energy is generated by engaging an ultrasonic transducer with said elongated member, and imparting vibrations emanating from said transducer to said elongated member, said vibrations having a frequency and intensity sufficient for transmitting said vibrations along a length of said elongated member into said fluid reservoir, and for breaking up said foreign material in said fluid reservoir.

7. The method of claim 1, wherein said elongated member comprises a solid probe.

8. The method of claim 2, wherein a flushing fluid is transmitted into said fluid reservoir to assist break up of the foreign material into said particulates, and suction is introduced into said fluid reservoir to extract said particulates.

9. The method of claim 2, wherein said particulates are removed by introducing suction into said fluid reservoir to extract particulates of said foreign material.

10. The method of claim 4, wherein said needle second end communicates with said source for flushing fluid, and said cannula second end communicates with said source of suction.

11. The method of claim 6, wherein said transducer is formed from a ceramic material.

12. The method of claim 6, wherein said elongated member comprises stainless steel.

13. The method of claim 8, wherein said flushing fluid is transmitted into said fluid reservoir through a bore in said elongated member.

14. The method of claim 8, wherein said elongated member comprises a hollow needle having said first and second ends, and wherein said second needle end is engaged with an outlet end of a syringe, said syringe comprising a plunger and a barrel, said barrel comprising said flushing fluid and being in fluid communication with said outlet end; said method further comprising the steps of transmitting the flushing fluid through the needle into the fluid reservoir via a downstroke of said plunger, and removing said particulates into said barrel via suction resulting from an upstroke of said plunger.

15. The method of claim 9, wherein the suction is introduced through a bore in said elongated member.

16. The method of claim 14, wherein said flushing fluid comprises heparinized saline.

* * * * *